United States Patent [19]

Nakada et al.

[11] Patent Number: 5,608,128
[45] Date of Patent: Mar. 4, 1997

[54] PRODUCTION METHODS OF 1,1,1,4,4,4-HEXSFLUORO-2-BUTENE COMPOUNDS AND 1,1,1,4,4,4,-HEXAFLUOROBUTANE

[75] Inventors: Tatsuo Nakada; Hirokazu Aoyama; Seiji Takubo, all of Settsu, Japan

[73] Assignee: Daikin Industries, Ltd., Osaka, Japan

[21] Appl. No.: 495,662

[22] PCT Filed: Jan. 19, 1994

[86] PCT No.: PCT/JP94/00068

§ 371 Date: Jul. 27, 1995

§ 102(e) Date: Jul. 27, 1995

[87] PCT Pub. No.: WO94/17020

PCT Pub. Date: Aug. 4, 1994

[30] Foreign Application Priority Data

Jan. 29, 1993 [JP] Japan .................... 5-034504

[51] Int. Cl.$^6$ .................. C07C 17/013; C07C 19/08; C07C 21/04; C07C 21/18
[52] U.S. Cl. ............................. 570/175; 570/153
[58] Field of Search ..................... 570/153, 175

[56] References Cited

U.S. PATENT DOCUMENTS 4,081,487  3/1978  Anello et al. ................. 570/153
4,110,406  8/1978  Anello et al. ................. 570/153
4,902,839  2/1990  Bielefeldt et al. ............. 570/175
5,364,991  11/1994 Seki et al. .................... 570/175

*Primary Examiner*—Joseph E Evans
*Attorney, Agent, or Firm*—Armstrong, Westerman, Hattori, McLeland & Naughton

[57] ABSTRACT

The present invention provides a production method of obtaining the mixture of 1,1,1,4,4,4-hexafluoro-2,3-dichloro-2-butene, 1,1,1,4,4,4-hexafluoro-2-chloro-2-butene and 1,1,1,4,4,4-hexafluoro-2-butene (1,1,1,4,4,4-hexafluoro-2-butene compounds) by reacting at least one of butane, butene and butadiene with chlorine and HF in the presence of a suitable catalyst, and also a production method of obtaining 1,1,1,4,4,4-hexafluorobutane by reducing said products in the presence of a noble metal catalyst. According to these methods, 1,1,1,4,4,4-hexafluorobutane, a compound useful for a blowing agent, cleaning agent or heating medium as an alternative to HCFC, can be obtained at a high selectivity rate; and 1,1,1,4,4,4-hexafluoro-2-butene compounds including 1,1,1,4,4,4-hexafluoro-2,3-dichloro-2-butene, 1,1,1,4,4,4-hexafluoro-2-chloro-2-butene and 1,1,1, 4,4,4-hexafluoro-2-butene, which are obtained as reaction intermediates in the production method of 1,1,1,4,4,4-hexafluorobutane and can be used as industrial intermediate chemicals for medicine and agricultural chemicals, can be produced less costly at high yields in a single step process.

10 Claims, No Drawings

PRODUCTION METHODS OF 1,1,1,4,4,4-HEXSFLUORO-2-BUTENE COMPOUNDS AND 1,1,1,4,4,4,-HEXAFLUOROBUTANE

This application is a 371 of PCT/JP94/00068 filed Jan. 19, 1994.

INDUSTRIAL APPLICATION

The present invention relates to production methods of 1,1,1,4,4,4-hexafluorobutane, which is a compound useful for a blowing agent, cleaning agent or heating medium as an alternative to HCFC; and 1,1,1,4,4,4-hexfluoro-2-butene compounds including 1,1,1,4,4,4hexafluoro-2,3-dichloro-2-butene, 1,1,1,4,4,4-hexafluoro-2-chloro-2-butene and 1,1,1,4,4,4-hexafluoro-2-butene, which are obtained as reaction intermediates in the production method of 1,1,1,4,4,4-hexafluorobutane and can be used as industrial intermediate chemicals for medicine and agricultural chemicals.

PRIOR ART

It is well known that 1,1,1,4,4,4-hexafluoro-2,3-dichloro-2-butene can be synthesized by chlorinating and fluorinating hexachlorobutadiene (U.S. Pat. No. 3149170). It is also well known that 1,1,1,4,4,4-hexafluoro-2-chloro-2-butene is produced by fluorinating hexachloro-1,3-butadiene with HF in the presence of antimony halide (Japanese Patent Opening No.50830/89).

In the known methods, however, hexachlorobutadiene used as a material is so expensive that there may be difficulties in procuring the raw material in bulk.

OBJECTIVES OF THE INVENTION

The objectives of the present invention are to provide a less costly industrial production method of 1,1,1,4,4,4-hexafluoro-2,3-dichloro-2-butene, 1,1,1,4,4,4-hexafluoro-2-chloro-2-butene and 1,1,1,4,4,4-hexafluoro-2butene, and also to provide a less costly industrial production method of 1,1,1,4,4,4-hexafluorobutane through a reduction of those compounds.

CONSTITUENTS OF THE INVENTIONS

As a result of thorough study to establish an industrially useful and inexpensive production method of 1,1,1,4,4,4-hexafluoro-2,3-dichloro-2-butene, 1,1,1,4,4,4-hexafluoro-2-chloro-2-butene and 1,1,1,4,4,4-hexafluoro-2butene, and also to establish a production method of 1,1,1,4,4,4-hexafluorobutane from those mixtures, the inventors have found that a mixture of 1,1,1,4,4,4-hexafluoro-2,3-dichloro-2-butene, 1,1,1,4,4,4-hexafluoro-2-chloro-2-butene and 1,1,1,4,4,4-hexafluoro-2-butene (1,1,1,4,4,4-hexafluoro-2-butene compounds), which are objective substances, is produced in a single step process at a high yield by reacting at least one of butane, butene and butadiene, which are easily procured at low prices, with chlorine and HF in the presence of a proper catalyst, and also that 1,1,1,4,4,-hexafluorobutane is obtained at a higher selectivity rate by reducing those products in the presence of a noble metal catalyst. As a result, the inventors have completed the present invention.

In the methods of the present invention, butane, butene and butadiene can be used each alone or together as a mixture for a material. Partially chlorinated and/or fluorinated butane, butadiene and 2-butene as reaction intermediates can be used by separating from reaction products. It is also possible to synthesize chlorinated and/or fluorinated butane, butadiene and 2-butene by a different method to use for the reaction.

For the catalyst in the reaction, a metal fluoride and/or metal oxyfluoride produced by fluorinating with HF the oxide of a metal (e.g., chromium) deposited from a metal salt solution by means of an alkali can be used. For the metal salt, hydrochloride or nitrate can be used. For the alkali, ammonia, urea or metal hydroxides can be used.

For the metal, one or mixed two or more of aluminum, chromium, manganese, nickel, cobalt, iron and zinc can be used. A metal fluoride obtained by fluorinating one of the halides of said metals and/or the metal oxyfluoride obtained by oxidizing said metal fluoride can be used too.

That metal fluoride can be used alone or as held in a proper carrier. The only condition for such a carrier is that it does not affect the catalytic activity in the process of the methods. Examples of such a carrier are active carbon and aluminum fluoride.

The reaction temperature can be in the range of 250° C. to 450° C., but lower temperatures are not practical because the reaction is slow at such a temperature. Accordingly, 300° C. to 400° C. is preferable.

While the reaction is exothermic, the reaction temperature can be easily controlled by properly setting the quantities of HF and the intermediates recycled.

The ratio of 1,1,1,4,4,4-hexafluoro-2,3-dichloro-2-butene, 1,1,1,4,4,4-hexafluoro-2-chloro-2-butene and 1,1,1, 4,4,4-hexafluoro-2-butene produced is easily controllable with the selection of the reaction temperature, quantity of HF and quantity of chlorine. Accordingly, the reaction temperature, quantity of HF and quantity of chlorine must be properly decided to meet a targeted selectivity rate.

Generally, HF five (5) to fifty (50) times as much in mol as butane, butene or butadiene to be reacted is used, and chlorine eight (8) to eighty (80) times as much in mol as butane to be reacted is used. These are ratios for the reaction in a general sense. In the actual reaction, however, partially fluorinated and/or chlorinated butane or 2-butene is recycled. Therefore, the quantities of HF and chlorine must be increased/decreased according to the recycled quantity of butane or 2-butene.

In chlorinating-fluorinating butane, butene or butadiene, some products from partially incomplete reaction are yielded under some conditions, but such products can be separated through proper measures such as distillation and recycled into a reaction container.

It is preferable to remove such products from partially incomplete reaction and then to use as the raw material a mixture of 1,1,1,4,4,4-hexafluoro-2,3-dichloro-2-butene, 1,1,1,4,4,4-hexafluoro-2-chloro-2-butene and 1,1,1,4,4,4-hexafluoro-2-butene purely in substance to synthesize 1,1, 1,4,4,4-hexafluorobutane through the reduction process in the presence of a noble metal catalyst.

The noble metal catalyst used in this reducing reaction (hydrogenation) is preferably a noble metal held in a carrier in a conventional manner. Such a noble metal can be, for example, Pt or Pd. Such a carrier is preferable not to have any direct effect on the reaction, and can be, for example, aluminum or active carbon.

Hydrogen used for the hydrogenation is better to generally be one (1) to ten (10) times as much in mol as the above-stated mixture.

The reaction temperature for hydrogenation can be in the range of 20° C. to 300° C. At lower temperatures,butane mixed with chlorine is produced in the reaction; on the other hand, at higher temperatures, the reducing catalyst tends to lose effectiveness faster. Butane mixed with chlorine can however be separated through such a conventional method as distillation, and those substances can be recycled after the separation.

INDUSTRIAL APPLICABILITY

According to the methods of the present invention, a mixture of 1,1,1,4,4,4-hexafluoro-2,3-dichloro-2-butene, 1,1,1,4,4,4-hexafluoro-2-chloro-2-butene and 1,1,1,4,4,4-hexafluoro-2-butene(1,1,1,4,4,4-hexafluoro-2-butene compounds), which are objective substances, can be produced in a single step process at a high yield by reacting at least one of butane, butene and butadiene, which are easily procured at low prices, with chlorine and HF in the presence of a proper catalyst, and 1,1,1,4,4,4-hexafluorobutane can also be obtained at a higher selectivity rate by reducing those products in the presence of a noble metal catalyst.

EMBODIMENTS

Embodiments of the present invention are explained below, however, these do not place any restriction on the scope of the invention, but variations are possible on the basis of its technical concept.

EXAMPLE 1

Chromium oxide was conventionally prepared in pellets of 3 mm Φ×3 mm. After 50 cc of this catalyst were placed in a reaction tube, it was fluorinated with HF. After the temperature of the reaction tube was adjusted to 350° C., HF at a rate of 500 cc/min and chlorine at a rate of 200 cc/min, both in gaseous state, were introduced into the tube, and then n-butane at a rate of 20 cc/min was introduced into the tube. The reaction products were washed with water and analyzed through GLC.

The selectivity rates of the products are shown in Table 1 below.

TABLE I

| Products | Selectivity |
|---|---|
| $CF_3CH=CHCF_3$ | 23.3% |
| $CF_3CH=CClCF_3$ | 38.4% |
| $CF_3CCl=CClCF_3$ | 28.1% |
| Other intermediates | 10.2% |

EXAMPLE 2

Aluminum oxide was conventionally prepared in pellets of 3 mm Φ×3 mm. After 50 cc of this catalyst were placed in a reaction tube, it was fluorinated with HF. After the temperature of the reaction tube was adjusted to 350° C., HF at a rate of 500 cc/min and chlorine at a rate of 200 cc/min, both in gaseous state, were introduced into the tube, and then n-butane at a rate of 20 cc/min was introduced into the tube. The reaction products were washed with water and analyzed through GLC.

The selectivity rates of the products are shown in Table 2 below.

TABLE 2

| Products | Selectivity |
|---|---|
| $CF_3CH=CClCF_3$ | 21.0% |
| $CF_3CH=CClCF_3$ | 38.4% |
| $CF_3CCl=CClCF_3$ | 19.5% |
| Other intermediates | 21.1% |

EXAMPLE 3

Manganese oxide was conventionally prepared in pellets of 3 mm Φ×3 mm. After 50 cc of this catalyst were placed in a reaction tube, it was fluorinated with HF. After the temperature of the reaction tube was adjusted to 350° C., HF at a rate of 500 cc/min and chlorine at a rate of 200 cc/min, both in gaseous state, were introduced into the tube, and then n-butane at a rate of 20 cc/min was introduced into the tube. The reaction products were washed with water and analyzed through GLC.

The selectivity rates of the products are shown in Table 3 below.

TABLE 3

| Products | Selectivity |
|---|---|
| $CF_3CH=CHCF_3$ | 18.4% |
| $CF_3CH=CClCF_3$ | 37.8% |
| $CF_3CCl=CClCF_3$ | 18.3% |
| Other intermediates | 25.5% |

EXAMPLE 4

Nickel oxide was conventionally prepared in pellets of 3 mmΦ×3 mm. After 50 cc of this catalyst were placed in a reaction tube, it was fluorinated with HF. After the temperature of the reaction tube was adjusted to 350° C., HF at a rate of 500 cc/min and chlorine at a rate of 200 cc/min, both in gaseous state, were introduced into the tube, and then n-butane at a rate of 20 cc min was introduced into the tube. The reaction products were washed with water and analyzed through GLC.

The selectivity rates of the products are shown in Table 4 below.

TABLE 4

| Products | Selectivity |
|---|---|
| $CF_3CH=CHCF_3$ | 16.5% |
| $CF_3CH=CClCF_3$ | 37.5% |
| $CF_3CCl=CClCF_3$ | 17.5% |
| Other intermediates | 28.5% |

EXAMPLE 5

Cobalt oxide was conventionally prepared in pellets of 3 mmΦ×3 mm. After 50 cc of this catalyst were placed in a reaction tube, it was fluorinated with HF. After the temperature of the reaction tube was adjusted to 350° C., HF at a rate of 500 cc min and chlorine at a rate of 200 cc/min, both in gaseous state, were introduced into the tube, and then n-butane at a rate of 20 cc min was introduced into the tube. The reaction products were washed with water and analyzed through GLC. The selectivity rates of the products are shown in Table 5 below.

TABLE 5

| Products | Selectivity |
| --- | --- |
| $CF_3CH=CHCF_3$ | 17.8% |
| $CF_3CH=CClCF_3$ | 29.7% |
| $CF_3CCl=CClCF_3$ | 15.0% |
| Other intermediates | 37.5% |

EXAMPLE 6

10 g of the catalyst of Pd held at a rate of 1 weight% in coconut shell active carbon were placed in a reaction tube and activated with hydrogen. While the reaction temperature in the tube was maintained at 150 °C., a mixture of three butene compounds obtained in Example 1 was introduced at a rate of 100 cc/min and hydrogen also introduced at a rate of 300 cc/min.

The reaction products were washed with water and analyzed through GLC. The selectivity rates of the products are shown in Table 6 below.

TABLE 6

| Products | Selectivity |
| --- | --- |
| $CF_3CH_2CH_2CF_3$ | 95.4% |
| $CF_3CHClCH_2CF_3$ | 2.2% |
| $CF_3CHClCHClCF_3$ | 2.4% |

EXAMPLE 7

10 g of the catalyst of Pt held at a rate of 1 weight% in coconut shell active carbon were placed in a reaction tube and activated with hydrogen. While the reaction temperature in the tube was maintained at 150° C., a mixture of three butene compounds obtained in Example 1 was introduced at a rate of 100 cc/min and hydrogen also introduced at a rate of 300 cc min.

The reaction products were washed with water and analyzed through GLC. The selectivity rates of the products are shown in Table 7 below.

TABLE 7

| Products | Selectivity |
| --- | --- |
| $CF_3CH_2CH_2CF_3$ | 91.6% |
| $CF_3CHClCH_2CF_3$ | 4.1% |
| $CF_3CHClCHClCF_3$ | 4.3% |

EXAMPLE 8

Chromium oxide was conventionally prepared in pellets of 3 mmΦ×3 mm. After 50 cc of this catalyst were placed in a reaction tube, it was fluorinated with HF. After the temperature of the reaction tube was adjusted to 350° C., HF at a rate of 500 cc min and chlorine at a rate of 200 cc min, both in gaseous state, were introduced into the tube, and then butadiene at a rate of 20 cc min was introduced into the tube. The reaction products were washed with water and analyzed through GLC.

The selectivity rates of the products are shown in Table 8 below.

TABLE 8

| Products | Selectivity |
| --- | --- |
| $CF_3CH=CHCF_3$ | 15.5% |
| $CF_3CH=CClCF_3$ | 28.6% |
| $CF_3CCl=CClCF_3$ | 46.6% |
| Other intermediates | 9.3% |

EXAMPLE 9

Chromium oxide was conventionally prepared in pellets of 3 mmΦ×3 mm. After 50 cc of this catalyst were placed in a reaction tube, it was fluorinated with HF. After the temperature of the reaction tube was adjusted to 350° C., HF at a rate of 500 cc/min and chlorine at a rate of 200 cc/min, both in gaseous state, were introduced into the tube, and then 2-butene at a rate of 20 cc/min was introduced into the tube. The reaction products were washed with water and analyzed through GLC. The selectivity rates of the products are shown in Table 9 below.

TABLE 9

| Products | Selectivity |
| --- | --- |
| $CF_3CH=CHCF_3$ | 12.2% |
| $CF_3CH=CClCF_3$ | 21.7% |
| $CF_3CCl=CClCF_3$ | 46.8% |
| Other intermediates | 19.3% |

From the results shown in Tables 1 to 9, intermediate hexafluoro-2-butene compounds and objective hexafluorobutane can be obtained easily and at higher selectivity rates according to the reaction based on the present invention.

We claim:

1. A production method of 1,1,1,4,4,4-hexafluoro-2-butene compounds including 1,1,1,4,4,4-hexafluoro-2,3-dichloro-2-butene, 1,1,1,4,4,4-hexafluoro-2-chloro-2-butene and 1,1,1,4,4,4-hexafluoro-2-butene characterized by reacting at least one of butane, butene and butadiene in the gaseous phase with chlorine and hydrogen fluoride in the presence of a catalyst.

2. A production method as stated in claim 1 where the catalyst is fluoride(s) and/or oxyfluoride(s) of one or more metals selected from aluminum, chromium, manganese, nickel, cobalt, iron and zinc.

3. A production method as stated in claim 1 or 2 where the catalyst is fluoride(s) and/or oxyfluoride(s) produced by fluorinating with hydrogen fluoride the oxide(s) of one or more metals selected from aluminum, chromium, manganese, nickel, cobalt, iron and zinc.

4. A production method as stated in claim 3 where the catalyst is a fluoride and/or an oxyfluoride produced by fluorinating chromium oxide with hydrogen fluoride.

5. A production method as stated in one of claims 1 or 2 where the reaction temperature is in the range of 250° C. to 450° C.

6. A production method of 1,1,1,4,4,4-hexafluorobutane by reducing a mixture of 1,1,1,4,4,4-hexafluoro-2,3-dichloro-2-butene, 1,1,1,4,4,4-hexafluoro-2-chloro-2-butene and 1,1,1,4,4,4-hexafluoro-2-butene obtained through the process of claim 1 in the presence of a noble metal catalyst.

7. A production method as stated in claim 6 where the reducing catalyst is a noble metal held in a carrier.

8. A production method as stated in claim 6 or 7 where the reduction reaction is carried out at a reaction temperature in the range of 20° C. to 300° C.

9. A production method as stated in claim 3 where the reaction temperature is in the range of 250° C. to 450° C.

10. A production method as stated in claim 4 where the reaction temperature is in the range of 250° C. to 450° C.

* * * * *

UNITED STATES PATENT AND TRADEMARK OFFICE
CERTIFICATE OF CORRECTION

PATENT NO.:    5,608,128
DATED      :    March 4, 1997
INVENTOR(S):   NAKADA et al.

It is certified that error appears in the above-identified patent and that said Letters Patent is hereby corrected as shown below:

On the Title Page, item [54], delete "HEXSFLUORO" and substitute -- HEXAFLUORO -- therefor.-- and col. 1, line 2, Signed and Sealed this Twenty-ninth Day of July, 1997

Attest:

BRUCE LEHMAN

*Attesting Officer*        *Commissioner of Patents and Trademarks*